United States Patent
Jeon et al.

(10) Patent No.: US 9,572,765 B2
(45) Date of Patent: Feb. 21, 2017

(54) COMPOSITION FOR PREVENTING HAIR LOSS OR PROMOTING HAIR RESTORATION, COMPRISING SOY EXTRACT

(75) Inventors: Hee Young Jeon, Yongin-si (KR); Seung Hun Kim, Yongin-si (KR); Su Kyung Kim, Yongin-si (KR); Hyun Jung Shin, Yongin-si (KR); Dae Bang Seo, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 0 days.

(21) Appl. No.: 14/124,602

(22) PCT Filed: Jun. 11, 2012

(86) PCT No.: PCT/KR2012/004599
§ 371 (c)(1),
(2), (4) Date: Dec. 6, 2013

(87) PCT Pub. No.: WO2012/169860
PCT Pub. Date: Dec. 13, 2012

(65) Prior Publication Data
US 2014/0093470 A1    Apr. 3, 2014

(30) Foreign Application Priority Data

Jun. 9, 2011  (KR) .................... 10-2011-0055597

(51) Int. Cl.
| | | |
|---|---|---|
| *A61K 8/97* | (2006.01) | |
| *A61Q 7/00* | (2006.01) | |
| *A61Q 5/00* | (2006.01) | |
| *A61Q 7/02* | (2006.01) | |

(52) U.S. Cl.
CPC . *A61K 8/97* (2013.01); *A61Q 5/00* (2013.01); *A61Q 7/00* (2013.01); *A61Q 7/02* (2013.01)

(58) Field of Classification Search
CPC .............. A61K 8/97; A61Q 7/00; A61Q 5/00; A61Q 7/02
See application file for complete search history.

(56) References Cited

U.S. PATENT DOCUMENTS

2009/0104295 A1* 4/2009 Kohno ................ 424/757

FOREIGN PATENT DOCUMENTS

| CN | 101115493 | | 1/2008 | | |
|---|---|---|---|---|---|
| CN | 101254274 | | 9/2008 | | |
| CN | 101757013 | | 6/2010 | | |
| JP | 59101414 | * | 6/1984 | ............... | A61K 7/06 |
| JP | 59101414 A | * | 6/1984 | ............... | A61K 7/06 |
| JP | 2005-119996 | | 5/2005 | | |
| KR | 10-2005-0075474 | | 7/2005 | | |
| KR | 10-2008-0032127 | | 4/2008 | | |
| KR | 10-2010-0045045 | | 5/2010 | | |
| KR | 10-2010-0080991 | | 7/2010 | | |

OTHER PUBLICATIONS

Written Opinion-PCT/KR2012/004599 dated Jan. 2, 2013.
International Search Report-PCT/KR2012/004599 dated Jan. 2, 2013.
Chinese Office Action-CN 201280038928.8 dated Feb. 15, 2015, citing CN101254274, CN101115493 and "Extraction of Soy isoflavones."
Ryang So Hwa, "Extraction of Soy isoflavones", General use of Plant oil resource, Dong-nam University, pp. 309-310, 2009.
Chinese Office Action-CN Application No. 201280038923.8 dated Nov. 5, 2015, citing the references listed within.
Jing Legang, et al., "Physical and Chemical Properties of Soybean Isoflavones", Chinese Agricultural Science Bulletin, vol. 22, No. 1, Jan. 2006, pp. 85-87.

* cited by examiner

*Primary Examiner* — Nannette Holloman
(74) *Attorney, Agent, or Firm* — Cantor Colburn LLP

(57) ABSTRACT

Disclosed is a composition for preventing hair loss or promoting hair restoration and for enhancing hair health, the composition comprising an active ingredient in the form of soy extract extracted using a $C_1$ to $C_5$ alcohol at a concentration of between 1% and 70% (v/v).

6 Claims, 1 Drawing Sheet

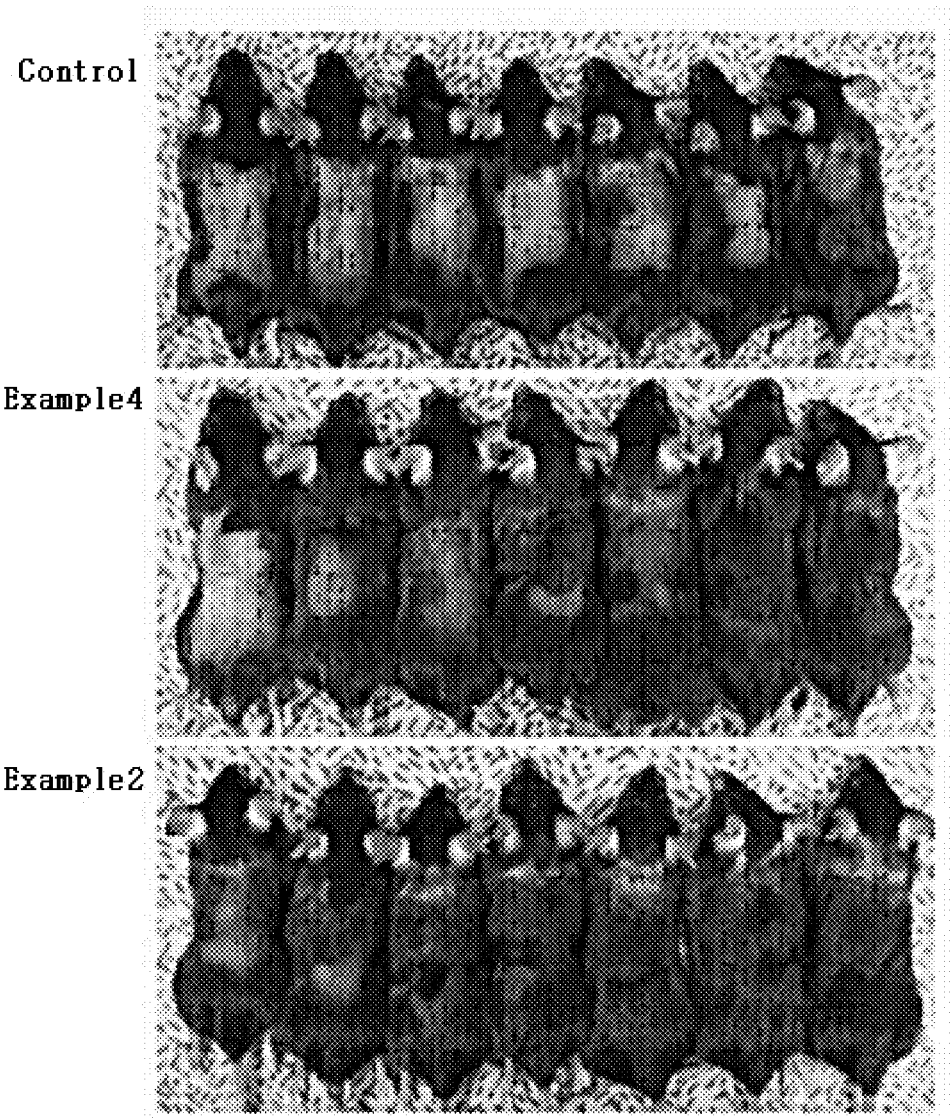

COMPOSITION FOR PREVENTING HAIR LOSS OR PROMOTING HAIR RESTORATION, COMPRISING SOY EXTRACT

TECHNICAL FIELD

The present disclosure relates to a composition for preventing hair loss or enhancing hair growth including a bean extract.

BACKGROUND ART

Whereas most animals shed and regrow hair seasonally, humans shed about 100 strands of hair out of about 100,000 strands and about 100 strands regrow every day, thus always maintaining a similar number.

The hair growth cycle consists of anagen, catagen and telogen phases. During the anagen phase, hair growth is promoted as cell division occurs actively in the hair papilla. Hair grows only in this stage. Considering that the anagen is about 3-5 years for men and about 4-6 years for women, about 80-85% of hair is in the anagen phase. In the catagen phase, which lasts about 3-4 weeks, the cell division declines gradually. Lastly, in the telogen phase, the hair papilla is withdrawn and the hair separated from the capillary vessel and simply stuck in the scalp. This lasts about 3 months and the hair in the telogen phase is easily lost upon physical stimulation.

DISCLOSURE

Technical Problem

The present disclosure is directed to providing a composition for preventing hair loss or enhancing hair growth and enhancing hair health.

Technical Solution

In a general aspect, there is provided a composition for preventing hair loss or enhancing hair growth, including a bean extract extracted with 1-70% (v/v) $C_1$-$C_5$ alcohol as an active ingredient.

In another general aspect, there is provided a composition for enhancing hair health, including a bean extract extracted with 1-70% (v/v) $C_1$-$C_5$ alcohol as an active ingredient.

In another general aspect, there is provided a cosmetic, food or pharmaceutical composition including the composition.

Advantageous Effects

The composition according to the present disclosure, which includes a bean extract extracted with a lower alcohol, specifically a lower alcohol at low concentration, as an active ingredient, nourishes the epithelial cells of the hair bulb by improving blood circulation in capillary vessels and induces activation of hair papilla cells by stimulating the hair bulb. Accordingly, the composition is effective in preventing hair loss, enhancing hair growth, preventing aging of hair and scalp and enhancing hair health. In particular, it exhibits excellent effect of promoting hair growth by facilitating the transition from telogen to anagen of the hair.

DESCRIPTION OF DRAWING

FIG. 1 shows hair growth in mice treated with bean extracts.

BEST MODE

As used herein, the term "hair loss" refers to loss of hair from the scalp or thinning of hair. The term "prevention of hair loss" refers to prevention and inhibition of the hair loss. And, the term "enhancement of hair growth" refers to enhancement of growth of new hair or healthy growth of existing hair.

Hair growth is affected by various factors including environmental factors such as temperature or sunlight, nutritional status of individuals and presence/absence of diseases, hormones, childbirth, exposure to radiation or various drugs, and so forth. The main causes of hair loss can be largely divided into internal physiological factors and external environmental factors. The internal physiological factors include, for example, increased activity of 5-alpha reductase which increases sebum secretion by converting testosterone, an androgen, into dihydrotestosterone (DHT). The external environmental factors include, for example, malnutrition of the hair bulb owing to insufficient blood circulation caused by constriction of blood vessels, dryness of the scalp, or the like. Accordingly, in order to prevent hair loss and enhance hair growth, it is necessary to nourish the hair bulb by dilating blood vessels, supply substances that serve the same function as the constituents of hair directly to the hair bulb, remove excess sebum around the hair bulb using a cleanser or an anti-sebum agent, or prevent dryness of the scalp using a moisturizer.

It is known that vitamin E, unsaturated fatty acid or anthocyanin included in beans such as black bean can dilate blood vessels and thus can improve blood circulation. Until recently, researches on bean have been focused mainly on isolation and purification of active ingredients that exhibit pharmacological activities, and few studies have been conducted on the medical use of the bean itself. Also, bean has been extracted mainly using high-concentration organic solvents as in the extraction of other natural products. The bean extract includes many unknown ingredients other than those identified, and some of them may exhibit useful pharmacological effects in the human body. Also, the useful ingredients may not be extracted by the common extraction methods using high-concentration organic solvents. The inventors of the present disclosure have extracted bean using low-concentration organic solvents as extraction solvent unlike the general extraction methods used to extract natural products, and have found out that the resulting extract exhibits stronger effect of preventing hair loss or enhancing hair growth and enhancing hair health than the extracts extracted using high-concentration organic solvents.

In an aspect, the present disclosure provides a composition for hair, specifically a composition for preventing hair loss or enhancing hair growth and a composition for enhancing hair health, including a bean extract extracted with 1-70% (v/v) $C_1$-$C_5$ alcohol as an active ingredient. The bean extract provides the effect of promoting proliferation of hair papilla cells by activating them and in nourishing the hair bulb by dilating capillary vessels and thus improving blood circulation. Also, it facilitates the transition from telogen to anagen of hair. Accordingly, the composition according to the present disclosure including the bean extract as an active ingredient may prevent hair loss, enhance hair growth and enhance hair health by preventing aging of hair, improving hair gloss and strengthening the hair bulb.

In an exemplary embodiment of the present disclosure, the composition includes a bean extract extracted using a low-concentration organic solvent as an active ingredient. In another exemplary embodiment of the present disclosure, the organic solvent includes $C_1$-$C_5$ alcohol. The $C_1$-$C_5$ alcohol may be one or more selected from a group consisting of, for example, methanol, ethanol, isopropyl alcohol, n-propyl alcohol, n-butanol and isobutanol, and specifically ethanol, although not being limited thereto. In another exemplary embodiment of the present disclosure, the concentration of the $C_1$-$C_5$ alcohol may be 1-70% (v/v), specifically 1-40% (v/v), more specifically 5-30% (v/v), further more specifically 12-25% (v/v).

In an exemplary embodiment of the present disclosure, the bean includes any bean the extract of which is effective in preventing hair loss, enhancing hair growth or enhancing hair health. In another exemplary embodiment of the present disclosure, the bean includes black bean or colored bean. In another exemplary embodiment of the present disclosure, the bean includes one or more selected from a group consisting of black bean (*Glycine max* (L.) Merr.), wild soybean (*Glycine soja* Sieb. et Zucc), heuktae (*Glycine max* (L.) Merr.), hwangtae (yellow soybean) (*Glycine max* (L.) Merr.), green bean (*Glycine max* (L.) Merr.), kidney bean (*Phaseolus vulgaris* L.), earlookgangnangkong (mottled kidney bean) (*Phaseolus vulgaris* L.), ultarikong (garden bean) (*Phaseolus vulgaris* L), mung bean (*Phaseolus radiates*), red bean (*Phaseolus angularis* Wight), geodu (azuki bean) (*Phaseolus angularis* Wight), kongnamulkong (soybean for sprouting) (*Glycine max* (L.) Merr.), seonbikong (*Glycine soja* Sieb. et Zucc) and soybean (*Glycine max* (L.) Merr.).

As used herein, the term "black bean" collectively refers to bean whose skin exhibits black color. Examples of the black bean include black bean (*Glycine max* (L.) Merr.), wild soybean (*Glycine soja* Sieb. et Zucc), heuktae (*Glycine max* (L.) Merr.) etc., although not being limited thereto. The name of the black bean may vary depending on the region, classification, dialect, or the like. As used herein, the term "black bean extract" refers to a substance extracted from the black bean using various methods. For example, it includes the substance extracted using organic solvents and various fractions of the extracted substance.

As used herein, the term "colored bean" collectively refers to bean whose skin exhibits deep color, including black, yellow or blue color. Examples of the colored bean include black bean (*Glycine max* (L.) Merr.), wild soybean (*Glycine soja* Sieb. et Zucc), heuktae (*Glycine max* (L.) Merr.), hwangtae (yellow soybean) (*Glycine max* (L.) Merr.), green bean (*Glycine max* (L.) Merr.), kidney bean (*Phaseolus vulgaris* L.), earlookgangnangkong (mottled kidney bean)(*Phaseolus vulgaris* L.), ultarikong (garden bean) (*Phaseolus vulgaris* L), mung bean (*Phaseolus radiates*), red bean (*Phaseolus angularis* Wight), geodu (azuki bean) (*Phaseolus angularis* Wight), kongnamulkong (soybean for sprouting) (*Glycine max* (L.) Merr.), seonbikong (*Glycine soja* Sieb. et Zucc) and soybean (*Glycine max* (L.) Merr.) etc., although not being limited thereto. The name of the colored bean may vary depending on the region, classification, dialect, or the like. As used herein, the term "colored bean extract" refers to a substance extracted from the colored bean using various methods. For example, it includes the substance extracted using organic solvents and various fractions of the extracted substance.

In an exemplary embodiment of the present disclosure, the composition includes 0.001-90 wt %, specifically 1-70 wt %, more specifically 5-50 wt %, of the bean extract based on the total weight of the composition. If the content of the bean extract is lower, the effect desired by the present disclosure may not be exerted and the composition may be unsatisfactory in terms of stability and safety. Also, the above described range may be appropriate in terms of cost effectiveness.

In another aspect, the present disclosure provides a cosmetic composition including a composition including a bean extract extracted with 1-70% (v/v) $C_1$-$C_5$ alcohol.

The cosmetic composition may be provided in any formulation appropriate for topical application. For example, it may be provided in the form of solution, oil-in-water emulsion, water-in-oil emulsion, suspension, solid, gel, powder, paste, foam or aerosol. The formulations may be prepared according to methods commonly employed in the related art.

The cosmetic composition may include auxiliary ingredients that provide synergic effect in a range not negatively affecting the desired effect. The cosmetic composition according to the present disclosure may include a substance selected from a group consisting of vitamin, polypeptide, polysaccharide and sphingolipid. The cosmetic composition according to the present disclosure may further include a moisturizer, an emollient, a surfactant, a UV absorbent, an antiseptic, a sterilizer, an antioxidant, pH control agent, an organic/inorganic pigment, an aromatic, a cooling agent or an antiperspirant. The amount of these ingredients may be easily determined by those skilled in the art within a range not negatively affecting the purpose and effect of the present disclosure. The amount may be 0.01-5 wt %, specifically 0.01-3 wt %, based on the total weight of the composition.

In another aspect, the present disclosure provides a food composition including a composition including a bean extract extracted with 1-70% (v/v) $C_1$-$C_5$ alcohol.

The formulation of the food composition is not particularly limited. For example, it may be formulated into tablet, granule, drink, caramel, etc. Each formulation of the food composition may include, in addition to the active ingredient, various ingredients commonly used in the related art. Those ingredients may be selected by those skilled in the art without difficulty considering the particular formulation or purpose of use, and they may result in synergic effect when used together.

Determination of the administration dose of the active ingredient is within the level of those skilled in the art. A daily dose may be, for example, 0.1-5000 mg/kg/day, more specifically 50-500 mg/kg/day, although not being limited thereto. The administration dose will vary depending on various factors, including the age of the subject to be treated, physical condition, presence of complication(s), or the like.

In another aspect, the present disclosure provides a pharmaceutical composition including a composition including a bean extract extracted with 1-70% (v/v) $C_1$-$C_5$ alcohol. In an exemplary embodiment of the present disclosure, the pharmaceutical composition may be effective in preventing or treating hair loss, enhancing hair growth and enhancing hair health.

The pharmaceutical composition according to the present disclosure may be administered orally or parenterally, e.g., intrarectally, topically, transdermally, intravenously, intramuscularly, intraperitoneally or subcutaneously. Formulations for oral administration may include tablet, pill, soft or hard capsule, granule, powder, fine granule, liquid, emulsion or pellet, although not being limited thereto. Formulations for parenteral administration may include solution, suspension, emulsion, gel, injection, drop, suppository, patch or spray, although not being limited thereto. The formulations may be prepared easily according to methods commonly employed in the related art and may further include a surfactant, an excipient, a wetting agent, an emulsification promoter, a suspending agent, a salt or buffer for control of osmotic pressure, a colorant, a flavoring agent, a stabilizer, an antiseptic, a preservative or other commonly used adjuvants.

The administration dose of the active ingredient in the pharmaceutical composition according to the present disclosure will vary depending on the age, sex and body weight of the subject to be treated, physiological condition and severity thereof, route of administration or the prescriber's judgment. The determination of the dose based on these factors is within the level of those skilled in the art. A daily dose may be, for example, 0.1-5000 mg/kg/day, more specifically 50-500 mg/kg/day, although not being limited thereto.

Hereinafter, the present disclosure will be described in detail through examples, comparative examples and test examples. However, the following examples, comparative examples and test examples are for illustrative purposes only and it will be apparent to those of ordinary skill in the art that the scope of the present disclosure is not limited by them.

EXAMPLES 1-4

Preparation of Black Bean (*Glycine max* (L.) Merr.) 10%, 20%, 50% and 70% Ethanol Extracts 1 kg of dried black bean was immersed in 10 L of 10%, 20%, 50% and 70% (v/v) ethanol solution, respectively, at 50° C. After extracting 3 times under reflux for 5 hours, the extract was allowed to stand at room temperature for 12 hours. The extract was filtered, concentrated under reduced pressure and freeze-dried to obtain a powder sample. The yield was 7-20% and the prepared powder was kept at low temperature until use.

EXAMPLE 5

Preparation of Wild Soybean (*Glycine soja* Sieb. et Zucc) 20% Ethanol Extract 1 kg of dried wild soybean was immersed in 5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 6

Preparation of Kidney Bean (*Phaseolus vulgaris* L.) 20% Ethanol Extract 300 g of dried kidney bean was immersed in 1.5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 7

Preparation of Earlookgangnangkong (Mottled Kidney Bean) (*Phaseolus vulgaris* L.) 20% Ethanol Extract 300 g of dried earlookgangnangkong (mottled kidney bean) was immersed in 1.5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 8

Preparation of Kongnamulkong (Soybean for Sprouting) (*Glycine max* (L.) Merr.) 20% Ethanol Extract 300 g of dried kongnamulkong (soybean for sprouting) was immersed in 1.5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 9

Preparation of Hwangtae (Yellow Soybean) (*Glycine max* (L.) Merr.) 20% Ethanol Extract 1 kg of dried hwangtae (yellow soybean) was immersed in 5 L of 20% (v/v) ethanol solution at 60° C. After extracting 2 times under reflux for 3 hours, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 10

Preparation of Green Bean (*Glycine max* (L.) Merr.) 20% Ethanol Extract 300 g of dried green bean was immersed in 1.5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 11

Preparation of Ultarikong (Garden Bean) (*Phaseolus vulgaris* L) 20% Ethanol Extract 1 kg of dried ultarikong (garden bean) was immersed in 5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 12

Preparation of Soybean (*Glycine max* (L.) Merr.) 20% Ethanol Extract 1 kg of dried soybean was immersed in 5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 13

Preparation of Geodu (Azuki Bean) (*Phaseolus angularis* Wight) 20% Ethanol Extract 300 g of dried geodu (azuki bean) was immersed in 1.5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 14

Preparation of Red Bean (*Phaseolus angularis* Wight) 20% Ethanol Extract 300 g of dried red bean was immersed in 1.5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 15

Preparation of Heuktae (*Glycine max* (L.) Merr.) 20% Ethanol Extract 300 g of dried heuktae was immersed in 1.5 L of 20% (v/v) ethanol solution at 60° C. After extracting for 3 hours under reflux, the extract was allowed to stand at room temperature for a predetermined time. The extract was filtered, concentrated under reduced pressure and freeze-dried to obtain a powder sample. The yield was 3-15% and the prepared powder was kept at low temperature until use.

EXAMPLE 16

Preparation of Black Bean (*Glycine max* (L.) Merr.) Butanol Extract 25 g of the black bean 20% (v/v) ethanol extract obtained in Example 2 was dissolved in 250 mL of distilled water and extracted 2 times with 250 mL of n-butanol using a separatory funnel. The butanol layer was concentrated under reduced pressure and freeze-dried to obtain a sample. The yield was 5-15% and the prepared sample was kept at low temperature until use.

EXAMPLE 17

Preparation of Wild Soybean (*Glycine soja* Sieb. et Zucc) Butanol Extract 1 g of the wild soybean 20% (v/v) ethanol extract obtained in Example 5 was dissolved in 10 mL of distilled water and extracted 2 times with 10 mL of n-butanol using a separatory funnel. The butanol layer was concentrated under reduced pressure and freeze-dried to obtain a sample. The yield was 5-15% and the prepared sample was kept at low temperature until use.

EXAMPLE 18

Preparation of Ultarikong (Garden Bean) (*Phaseolus vulgaris* L) Butanol Extract 25 g of the garden green bean 20% (v/v) ethanol extract obtained in Example 11 was dissolved in 250 mL of distilled water and extracted 2 times with 250 mL of n-butanol using a separatory funnel. The butanol layer was concentrated under reduced pressure and freeze-dried to obtain a sample. The yield was 5-15% and the prepared sample was kept at low temperature until use.

EXAMPLE 19

Preparation of Green Bean (*Glycine max* (L.) Merr.) Butanol Extract 1 g of the green bean 20% (v/v) ethanol extract obtained in Example 10 was dissolved in 10 mL of distilled water and extracted 2 times with 10 mL of n-butanol using a separatory funnel. The butanol layer was concentrated under reduced pressure and freeze-dried to obtain a sample. The yield was 5-15% and the prepared sample was kept at low temperature until use.

EXAMPLE 20

Preparation of Hwangtae (Yellow Soybean) (*Glycine max* (L.) Merr.) Butanol Extract 1 g of the hwangtae (yellow soybean) 20% (v/v) ethanol extract obtained in Example 9 was dissolved in 10 mL of distilled water and extracted 2 times with 10 mL of n-butanol using a separatory funnel. The butanol layer was concentrated under reduced pressure and freeze-dried to obtain a sample. The yield was 5-15% and the prepared sample was kept at low temperature until use.

EXAMPLE 21

Preparation of Kongnamulkong (Soybean for Sprouting) (*Glycine max* (L.) Merr.) Butanol Extract 1 g of the kongnamulkong (soybean for sprouting) 20% (v/v) ethanol extract obtained in Example 8 was dissolved in 10 mL of distilled water and extracted 2 times with 10 mL of n-butanol using a separatory funnel. The butanol layer was concentrated under reduced pressure and freeze-dried to obtain a sample. The yield was 5-15% and the prepared sample was kept at low temperature until use.

EXAMPLE 22

Preparation of Soybean (*Glycine max* (L.) Merr.) Butanol Extract 25 g of the soybean 20% (v/v) ethanol extract obtained in Example 12 was dissolved in 250 mL of distilled water and extracted 2 times with 250 mL of n-butanol using a separatory funnel. The butanol layer was concentrated under reduced pressure and freeze-dried to obtain a sample. The yield was 5-15% and the prepared sample was kept at low temperature until use.

EXAMPLE 23

Preparation of Kidney Bean (*Phaseolus vulgaris* L.) Butanol Extract 1 g of the kidney bean 20% (v/v) ethanol extract obtained in Example 6 was dissolved in 10 mL of distilled water and extracted 2 times with 10 mL of n-butanol using a separatory funnel. The butanol layer was concentrated under reduced pressure and freeze-dried to obtain a sample. The yield was 5-15% and the prepared sample was kept at low temperature until use.

COMPARATIVE EXAMPLE 1

Preparation of Black Bean (*Glycine max* (L.) Merr.) Extract Using Water 1 kg of dried black bean was immersed in 10 L of water at 100° C. After extracting 3 times under reflux for 5 hours, the extract was allowed to stand at room temperature for 12 hours. The extract was filtered, concentrated under reduced pressure and freeze-dried to obtain a powder sample. The yield was 7-20% and the prepared powder was kept at low temperature until use.

COMPARATIVE EXAMPLE 2

Preparation of Black Bean (*Glycine max* (L.) Merr.) Extract Using 75% Ethanol 1 kg of dried black bean was immersed in 10 L of 75% (v/v) ethanol solution at 50° C. After extracting 3 times under reflux for 5 hours, the extract was allowed to stand at room temperature for 12 hours. The extract was filtered, concentrated under reduced pressure and freeze-dried to obtain a powder sample. The yield was 7-20% and the prepared powder was kept at low temperature until use.

COMPARATIVE EXAMPLE 3

Preparation of Black Bean (*Glycine max* (L.) Merr.) Extract Using 100% Ethanol

A black bean extract was prepared in a manner substantially the same as in Comparative Example 2 except for using 100% (v/v) ethanol. The yield was 7-20% and the prepared powder was kept at low temperature until use.

TEST EXAMPLE 1

Proliferation of Hair Papilla Cells

The effect of the bean extract on the proliferation of hair papilla cells was evaluated using rat vibrissa dermal papilla cells (PVGDPLTt sa 6 obtained by transfecting PVG rat vibrissa dermal papilla cells with the polyomavirus large T gene encoded with the temperature-sensitive T-antigen. Hereinafter, DP cells.).

First, DP cells were prepared on a 96-well plate, at a concentration of about $10^4$ cells/well. Each of the samples of Examples 1-4 and Comparative Examples 1-3 was dissolved in dimethyl sulfoxide (DMSO) or ethanol and serially diluted to a final concentration of 10 ppm using a DMEM medium containing 5% FBS serum. After adding 200 μL of the medium including the sample of Examples 1-4 or Comparative Examples 1-3 to each well, the cells were incubated for about 3 days in a 5% $CO_2$ incubator at 37° C. After adding 50 μL of 2 mg/mL MTT solution to each well, the cells were further incubated for 4 hours in the same incubator. After the MTT reagent was absorbed into the mitochondria of the cells, the supernatant was removed and 150 μL of DMSO was added. Then, the formazan dye was dissolved out by stirring for 10 minutes. Subsequently, O.D. value was measured at 515 nm using an ELISA reader, and the number of cells was counted using a standard curve. The ability of promoting proliferation of hair papilla cells (%) of the samples of Examples 1-4 and Comparative Examples 1-3 was calculated based on the number of cells. The result is shown in the following table.

TABLE 1

| | Comp. Ex. 1 | Comp. Ex. 2 | Comp. Ex. 3 | Ex. 1 | Ex. 2 | Ex. 3 | Ex. 4 |
| --- | --- | --- | --- | --- | --- | --- | --- |
| Ability of promoting proliferation of hair papilla cells (%) | 15.1 ± 1.0 | 18.8 ± 0.9 | 12.5 ± 0.4 | 24.6 ± 0.4 | 42.1 ± 1.2 | 28.8 ± 1.3 | 22.5 ± 1.4 |

As seen from the table, the samples of Examples 1-4 exhibited superior ability of promoting proliferation of hair papilla cells as compared to the sample extracted with water (Comparative Example 1) or those extracted with 75% and 100% (v/v) ethanol (Comparative Examples 2-3). In particular, the bean extract sample of Example 2 which was extracted with 20% ethanol showed the best effect of promoting proliferation of hair papilla cells. Accordingly, it can be seen that the bean extract extracted with alcohol exhibits excellent effect of preventing hair loss, enhancing hair growth and enhancing hair health by promoting the proliferation of hair papilla cells.

TEST EXAMPLE 2

Dilation of Capillary Vessels

Opening of the $K^+$ channel leads to activation of mitogenesis, relaxation of the vascular smooth muscle and dilation of blood vessels. Also, it is known that the closing of the $K^+$ channel prevents the proliferation of NIH3T3 fibroblasts. Accordingly, the opening of the $K^+$ channel and the dilation of blood vessels can be measured by monitoring the proliferation of NIH3T3 fibroblasts.

First, NIH3T3 fibroblasts were seeded onto a 24-well culture plate, at a concentration of $10^4$ cells/well, and incubated for 24 hours in a DMEM medium containing 10% fetal calf serum (FCS) and 2 mM L-glutamine and not containing antibiotics. The cells were further incubated for 72 hours after replacing the culture medium with one including each of the samples of Examples 1-4 and Comparative Examples 1 and 3. The media including the samples of Examples 1-4 and Comparative Examples 1 and 3 were prepared in the same manner as in Test Example 1. After removing the medium and washing with PBS (free of $Ca^{2+}/Mg^{2+}$), the cells were incubated after treating with 0.5 mL trypsin-ethylenediaminetetraacetic acid (TE). After adding DMEM containing 10% FCS, the cells were taken and centrifuged at 6000 rpm in an EP tube. After removing the supernatant, the remaining cell lysate was suspended in 100 µL of PBS and the number of cells was counted using a hemocytometer. The ability of dilating capillary vessels of the samples of Examples 1-4 and Comparative Examples 1 and 3 was calculated based on the number of cells. The result is shown in the following table.

TABLE 2

|  | Comp. Ex. 1 | Comp. Ex. 3 | Ex. 1 | Ex. 2 | Ex. 3 | Ex. 4 |
| --- | --- | --- | --- | --- | --- | --- |
| Ability of dilating capillary vessels (%) | 8.3 ± 1.2 | 4.3 ± 1.2 | 12.6 ± 4.4 | 34.1 ± 2.2 | 18.8 ± 3.1 | 22.5 ± 0.7 |

As seen from the table, the samples of Examples 1-4 exhibited superior ability of promoting proliferation of hair papilla cells as compared to the sample extracted with water (Comparative Example 1) or that extracted with 100% (v/v) ethanol (Comparative Example 3). In particular, the bean extract sample of Example 2 which was extracted with 20% ethanol showed the best effect of dilating capillary vessels. Accordingly, it can be seen that the bean extract extracted with alcohol exhibits excellent effect of enhancing hair health, preventing hair loss and enhancing hair growth by improving blood circulation to the capillary vessels of the scalp.

TEST EXAMPLE 3

Enhancement of Hair Growth

The effect of enhancing hair growth in mice was evaluated using the samples of Examples 2 and 4. First, the hair on the back of 47-53 days old mice (C57BL/6) was shaved using an electric clipper. The hair of the mice in this period is in the telogen phase and does not grow well. Among the mice, those with good skin status were grouped into 3 groups, with 5-7 mice per each group, and were kept in different cases. The mice were allowed free access to cereal feed containing the sample of Example 2 or 4 at a concentration of 0.6%. The mice in the control group were given cereal feed not containing the bean extract. 23 days later, the change of the shaved part was observed and the result is shown in FIG. 1. Also, the hair newly grown on the shaved part was collected using an electric clipper and weighed.

The result is shown in the following table.

TABLE 3

|  | Control | Example 2 | Example 4 |
| --- | --- | --- | --- |
| Hair weight (mg) | 32.1 ± 12.2 | 98.5 ± 8.4 | 56.1 ± 12.2 |

As seen from the table and FIG. 1, the bean extract samples extracted with ethanol promoted the growth of mouse hair. In particular, the bean extract sample of Example 2 which was extracted with 20% ethanol showed very superior effect of enhancing hair growth. Accordingly, it can be seen that the bean extract extracted with alcohol exhibits excellent effect of enhancing hair growth.

Hereinafter, the present disclosure will be described in detail through formulation examples. However, the following formulation examples are for illustrative purposes only and it will be apparent to those of ordinary skill in the art that the scope of the present disclosure is not limited by the formulation examples.

FORMULATION EXAMPLE 1

Soft Capsule 100 mg of black bean extract, 50 mg of soybean extract, 180 mg of soybean oil, 2 mg of palm oil, 8 mg of hydrogenated palm oil, 4 mg of yellow beeswax and 6 mg of lecithin are mixed and 400 mg of the mixture is filled in a capsule to prepare a soft capsule.

FORMULATION EXAMPLE 2

Tablet 100 mg of ultarikong (garden bean) extract, 100 mg of glucose, 96 mg of starch and 4 mg of magnesium stearate are mixed and 40 mg of 30% ethanol is added to form granule, which is dried at 60° C. and compounded into a tablet.

FORMULATION EXAMPLE 3

Drink 100 mg of wild soybean extract, 10 g of glucose, 2 g and citric acid and 187.8 g of purified water are mixed and filled in a bottle to a final volume of 200 mL.

FORMULATION EXAMPLE 4

Health Food

| Black bean extract | 1000 mg |
| --- | --- |
| Vitamin mixture | |
| Vitamin A acetate | 70 µg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 µg |
| Vitamin C | 10 mg |
| Biotin | 10 µg |
| Nicotinamide | 1.7 mg |
| Folic acid | 50 µg |
| Calcium pantothenate | 0.5 mg |

-continued

| Mineral mixture | |
|---|---|
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Calcium citrate | 90 mg |
| Calcium carbonate | 100 mg |
| Magnesium chloride | 24.8 mg |

Although the above-described composition of the vitamin and mineral extracts is given as a specific example adequate for health food, it may be altered otherwise. The above ingredients may be mixed and prepared into granule to prepare a health food composition.

FORMULATION EXAMPLE 5

Cream

A cream is prepared with the composition described in the following table.

TABLE 4

| Ingredients | Contents (wt %) |
|---|---|
| Heuktae extract | 3.0 |
| Glycerin | 3.0 |
| Butylene glycol | 3.0 |
| Liquid paraffin | 7.0 |
| Beta-glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |

TABLE 4-continued

| Ingredients | Contents (wt %) |
|---|---|
| Antiseptic, colorant and aromatic | Adequate |
| Purified water | Balance |

While the exemplary embodiments have been shown and described, it will be understood by those skilled in the art that various changes in form and details may be made thereto without departing from the spirit and scope of this disclosure as defined by the appended claims.

The invention claimed is:

1. A method for preventing hair loss or enhancing hair growth comprising administering an effective amount of an active ingredient consisting essentially of a black bean (*Glycine max* (L. Merr)) extract extracted with a 12% to 25% (v/v) ethanol solution to a subject in such need in order to prevent hair loss or enhance hair growth.

2. The method for preventing hair loss or enhancing hair growth according to claim 1, wherein the black bean extract is contained in a composition and the composition comprises 0.001-90 wt % of the black bean extract based on the total weight of the composition.

3. The method for preventing hair loss or enhancing hair growth to claim 1, wherein the black bean extract nourishes the hair bulb by improving blood circulation to the scalp.

4. The method for preventing hair loss or enhancing hair growth according to claim 1, wherein the black bean extract is contained in a composition and the composition is a cosmetic composition.

5. The method for preventing hair loss or enhancing hair growth according to claim 1, wherein the black bean extract is contained in a composition and the composition is a food composition.

6. The method for preventing hair loss or enhancing hair growth according to claim 1, wherein the black bean extract is contained in a composition and the composition is a pharmaceutical composition.

* * * * *